(12) United States Patent
Mohamed Hassan et al.

(10) Patent No.: US 8,552,026 B2
(45) Date of Patent: Oct. 8, 2013

(54) ISATIN DERIVATIVES, MEDICAMENTS CONTAINING THE ISATIN DERIVATIVES AND METHOD FOR ITS PREPARATION

(75) Inventors: Tarek Aboul-Fadl Mohamed Hassan, Riyadh (SA); Fayzah bint Ahmad S. Bin Jubair, Riyadh (SA)

(73) Assignee: King Saud University, Riyadh (SA)

( * ) Notice: Subject to any disclaimer, the term of this patent is extended or adjusted under 35 U.S.C. 154(b) by 301 days.

(21) Appl. No.: 13/081,521

(22) Filed: Apr. 7, 2011

(65) Prior Publication Data

US 2012/0259119 A1 Oct. 11, 2012
US 2013/0190498 A2 Jul. 25, 2013

(51) Int. Cl.
*A61K 31/44* (2006.01)
*C07D 471/04* (2006.01)

(52) U.S. Cl.
USPC .......................................... 514/300; 546/123

(58) Field of Classification Search
USPC .......................................... 546/123; 514/300
See application file for complete search history.

(56) References Cited

PUBLICATIONS

Aboul-Fadi et al., European Journal of Medicinal Chemistry (2010), 45(10), 4578-4586.*
Tarek et al., Int. J. Res. Pharm. Sci. vol. 1, Issue-2, 113-126, 2010.*
L. Ballell et al.; "New Small-Molecule Synthetic Antimycobacterials"; Antimicrobial Agents and Chemotherapy, Jun. 2005, pp. 2153-2163.
M.A. Hussein et al.; "Synthesis and Antitubercular Activity of Some Mannich Bases Derived from Isatin Isonicotinic Acid Hydrazone"; Bull. Pharm. Sci. Assiut University, vol. 28, Jun. 2005, pp. 131-136.
Adel F. Youssef et al.; "Design Synthesis and Antidepressant Activity of Some N2-Substituted Nalidixic Acid Hydrazides and Their Cyclized Analogues", Bull. Pharm. Sci. Assiut University, vol. 21 Jun. 1998, pp. 15-26.
L. Barth Reller et al.; "Susceptibility Testing for Mycobacteria"; Clinical Infectious Diseases (2000); 31:1209-1215.
Gail L. Woods et al.; "Susceptibility Testing of Mycobacteria, Nocardiae, and Other Aerobic Actinomycetes; Approved Standard"; vol. 23, No. 18; NCCLS Document M24-A (2003).
T. Aboul-Fadi et al.; "Synthesis, Antitubercular Activity and Pharmacokinetic Studies of Some Schiff Bases Derived from 1-Alkylisatin and Isonicotinic Acid Hydrazide (INH)"; Arch. Pharm. Res vol. 26 (2003) pp. 778-784.

\* cited by examiner

*Primary Examiner* — Niloofar Rahmani
(74) *Attorney, Agent, or Firm* — Renner, Otto, Boisselle & Sklar, LLP

(57) ABSTRACT

The present invention relates to an isatin derivative having the formula (I), a medicament for treatment of tuberculoses containing that isatin derivative as well as a method for preparing isatin derivative according to formula (I).

6 Claims, No Drawings

ISATIN DERIVATIVES, MEDICAMENTS CONTAINING THE ISATIN DERIVATIVES AND METHOD FOR ITS PREPARATION

BACKGROUND

Tuberculosis remains amongst the world's great public health challenges. Although drugs for treatment of tuberculosis (TB) have been available for nearly 50 years, TB remains a global health crisis, killing 2-3 million people annually and for a global economic toll of $12 billion each year. The recent emergence of multi drug-resistant (MDR) and extensively drug-resistant (XDR) tuberculosis resulted in a major setback in the global fight against TB. The prevailing situation is made worse by the continuous increase in the number of immune-compromised patients living with HIV who are more prone to TB and other bacterial infections. No new drugs have been developed specifically against mycobacteria since the 1960s and only within the last few years have some promising drug candidates emerged. Thus, more than ever, there is an urgent need to develop new anti-TB drugs to combat the spread of TB, particularly in its hard-to-kill multidrug-resistant, persistent and latent forms.

There are two basic approaches to develop a new drug for TB:
i) Synthesis of new analogues, modifications or derivatives of existing compounds for shortening and improving TB treatment.
ii) Searching for novel structures, that the TB organism has never been presented with before, for the treatment of MDR-TB.

Indoline-2,3-dione (isatin) derivatives have been reported to show antitubercular activities, see M. A. Hussein, T. Aboul-Fadl, A. Hussein, Bull. Pharm. Sci. Assiut Univ. 28 (2005) 131-136; L. Ballell, R. A. Field, K. Duncan, R. J. Young, Antimicrob. Agens Chemother. 49 (2005) 2153-2163. Isatin is considered as a versatile lead molecule for designing of potential anti tubercular agents.

SUMMARY

It is thus an object of the present invention to provide an anti-TB agent with improved properties such as enhanced activity against MDR strains, reduced toxicity, shortened duration of therapy, rapid mycobatericidal mechanism of action and the ability to penetrate host cells and exert antimycobacterial effects in the intracellular environment. Further, cross-resistance with current drugs should be avoided.

DETAILED DESCRIPTION

A new isatin derivative as promising anti-TB agent has been found having the following formula (I)

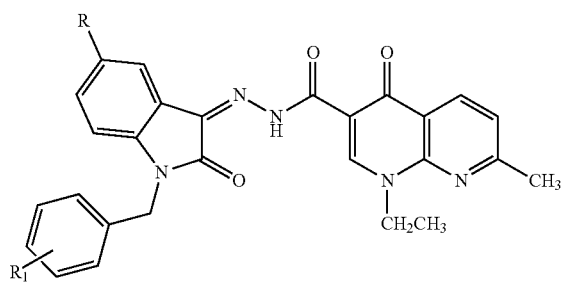

(I)

wherein R is selected from H, halogen, preferably Br, $CH_3$, $OCH_3$ and $NO_2$; and wherein $R_1$ is selected from H, halogen, preferably Br, $CH_3$, $OCH_3$ and $NO_2$.

Formula (I) may have from one to five substituents $R_1$, which may be same or different, preferably one substituent $R_1$.

Preferably, R and $R_1$ are both hydrogen.

According to the invention is also a medicament for treatment of tuberculosis containing an isatin derivative.

According to the invention is also a method for preparing an isatin derivative comprising the step of reacting a compound according to formula (II) with a compound according to formula (III) in an acidified alcoholic solvent, and isolating the compound according to formula (I):

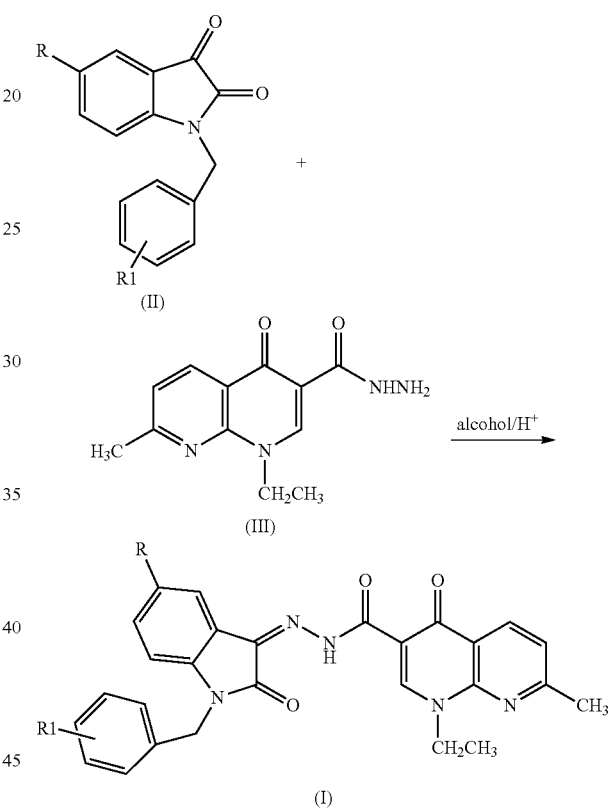

wherein R and $R_1$ are defined as above.

Finally, the reaction is preferably under reflux.

The compounds according to formula (I) are Schiff's bases of indoline-2,3-dione derivatives (isatin derivatives) and nalidixic acid carbohydroxide. This compounds show promising antimycobaterial acitivity in vitro, as will be demonstrated by the following detailed description.

The designed Schiff's bases can be obtained according to the above reaction scheme, i.e. by reacting an appropriate isatin derivative with a carbohydrazide of nalidixic acid.

Compounds according to formulae (II) and (III) can be prepared according to reported procedures, such as T. Aboul-Fadl, F. A. Mohammed, E. A. Hassan, Arch. Pharm. Res. 26 (2003) 778-784 and A. F. Youssef, F. A. Omar, H. A. Elsherief, G. E. A. A. Abuo-Rahma, Bull. Pharm. Sci. Assiut Univ. 21 (1998) 15-26. Compounds according to formulae (II) and (III) are described in literature, melting points and spectral data for these compounds are consistent with the reported ones.

A synthesis of Schiff's bases of isatin derivative and carbohydrzide of nalidixic acid to result in compounds according to formula (I) can be conducted as follows:

A stirred mixture of appropriate isatin derivative (compound II, 0.5 mmol) and carbohydrazide of nalidixic acid (compound III 0.12 g, 0.5 mmol) in ethanol as acidified with 4 drops of glacial acetic acid is refluxed for a specific time (4-13 hours), and the reaction progress is monitored by thin layer chromatography (TLC). The reaction mixture is then concentrated, cooled and filtered. The filtrate is either crystallized by an appropriate solvent or washed thoroughly with ethanol.

A compound according to formula (I) with R=H and $R_1$=H (N'-(1-benzyl-2-oxoindolin-3-ylidene)-1-ethyl-1,4-dihydro-7-methyl-4-oxo-1,8-naphthyridine-3-carbohydrazid was prepared and the following analytical data was received:

Yield: 55%; m.p. 292° C. (from DCM). $IRv_{max}/cm^{-1}$ 1441.03 (N—N), 1466.24, 1489.30 (C—N), 1510.87, 1541.11 (C=N), 1611.46, 1679.65 (C=O amidic), 2926.03 (C—H aliphatic), 3058.36 (C—H aromatic), 3446.27 (N—H). $^1H$ NMR $\delta_H(CDCl_3)$ 1.58 (3H, t, J=6,5, $N_1'CH_2CH_3$), 2.73 (3H, s, $C_7'CH_3$), 4.63 (2H, q, J=7.5, $N_1'CH_2CH_3$), 5.08 (2H, s, $N_1CH_2ph$), 6.76 (1H, d, $J_s$=8, $C_7H$), 7.12 (1H, t, J=7.5, $C_5H$), 7.29-7.39 (7H, m, $C_4H$, $C_6H$ and phenyl protons), 7.93 (1H, d, J=7.5, $C_6'H$), 8.88 (1H, d, J=8.5, $C_5'H$), 9.07 (1H, s, $C_2'H$), 15.42 (1H, s, CONH). $^{13}C$ NMR $\delta_C$ (DMSO-$d_6$): 15.38 ($N_1'CH_2CH_3$), 25.19 ($C_7'CH_3$), 43.44 ($N_1CH_2ph$). 47.07 ($N_1'CH_2CH_3$), 110.03 ($C_7$), 110.94 ($C_5'$), 120.01 ($C_{3a}$), 120.37 ($C_6'$), 121.43 ($C_{4a}'$), 121.92 ($C_5$), 122.27 ($C_4$), 127.39, 127.83, 128.93, 132.68, 135.73, 135.84 (phenyl carbons), 131.39 ($C_3'$), 136.45 ($C_3$), 137.69 ($C_6$), 144.03 ($C_2'$), 148.48 ($C_{8a}'$), 149.37 ($C_{7a}$), 163.12 ($C_2$), 163.72 ($C_7'$), 164.24 ($C_9'$), 176.55 ($C_4'$). MS m/z (%): 43.8 (100%), 90.7 (1.21%), 103.0 (6.91%), 104.1 (8.54%), 117.0 (7.58%), 131.2 (0.78%), 132.8 (22.71%), 145.8 (3.19%), 159.8 (8.66%), 173.1 (1.85%), 188.4 (2.32%), 201.9 (1.30%), 210.2 (6.92%), 214.5 (1.80%), 230.3 (1.16%), 231.4 (0.99%), 238.7 (0.54%), 246.8 (22.17%), 332.2 (3.31%), 346.2 (2.25%), 464.6 (0.45%), 465.8 (2.71%), 466.9 (2.25%).

The anti-TB activity of the synthesized compound was tested using the agar dilution method, see T. Aboul-Fadl, F. A. Mohammed, E. A. Hassan, Arch. Pharm. Res. 26 (2003) 778-784 and NCCLS Susceptibility Testing of Mycobacteria, Nocardia, and Other Aerobic Actinomycetes; Tentative Standard NCCLS document M24-T2 [ISBN 1-56238-423-6], second ed., NCCLS, 960 West Valley Road, Suite 1400, Wayne, Pa. 2000, 19087-1898, USA.

The synthesized compound was solubilized in DMSO at a concentration of 1 mg/ml. Appropriate amount was diluted first with 10% molten agar to give a concentration of 200 µg/ml. Further dilutions for the active compound were done to give 100, 50, 25, 12.5, 6.25 and up to 0.625 µg/ml. The agar and the compound solution were mixed thoroughly and the mixture was poured in Petri-dishes on a level surface to result in an agar depth of 3-4 mm and allowed to harden. The incula were prepared by growing overnight culture in Mueller-Hinton broth. The cultures were diluted 1:100. Test organisms were streaked in a radial pattern and plates were incubated at 35° C. for 48 hours. Control experiments consisted of the tested TB strains, DMSO and the growing media were treated in the same manner. Complete suspension of growth was observed prior to declaring the compound to be active. The synthesized compound was evaluated for the antimycobacterial activity in vitro again four Mycobacterium strains: *Mycobacterium intercellulari* (ATCC35743), *Mycobacterium xenopi* (ATCC 14470), *Mycobacterium cheleneo* (ATCC 35751) and *Mycobacterium smegmatis* (ATCC 35797) by the agar dilution method. Isoniazid (INH) was used as a reference drug and control experiments done using a growth media free from drugs or the tested compound. Results of the in vitro antitubercular activity on the tested compound along with standard drug for comparison are given in table 1. The data of the antitubercular activity screening revealed that for the inventive compound it was found to be 20 times more potent than the first line antitubercular drug INH in vitro.

TABLE 1

In vitro anti-TB activity of synthesized compounds

| | MIC (µg/ml)/Mycobacterium strain | | | |
| --- | --- | --- | --- | --- |
| Compound | M. intercellulari | M. xenopi | M. cheleneo | M. smegmatis |
| R = H; $R_1$ = H | 0.625 | 0.625 | 0.625 | 0.625 |
| INH | 12.5 | 12.5 | 12.5 | 12.5 |

The features disclosed in the foregoing description and in the claims may, both separately and in any combination thereof, be material for realizing the invention in diverse forms thereof.

The invention claimed is:

1. Isatin derivative according to the following formula (I)

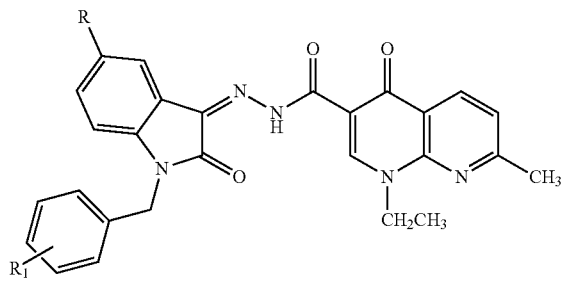

(I)

wherein R is selected from H, halogen, $CH_3$, $OCH_3$ and $NO_2$; and wherein $R_1$ is selected from H, halogen, $CH_3$, $OCH_3$ and $NO_2$.

2. Isatin derivative according to claim 1, wherein R and $R_1$ are both hydrogen.

3. Isatin derivative according to claim 1, wherein when R and $R_1$ are halogen, the halogen is Br.

4. Pharmaceutical composition for treatment of tuberculosis containing an isatin derivative according to claim 1.

5. Method for preparing an isatin derivative according to claim 1 comprising the step of reacting a compound according to formula (II) with a compound according to formula (III) in an acidified alcoholic solvent, and isolating the compound according to formula (I):

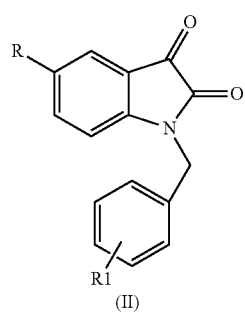
(II)
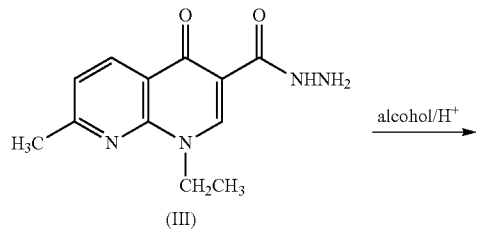
(III)
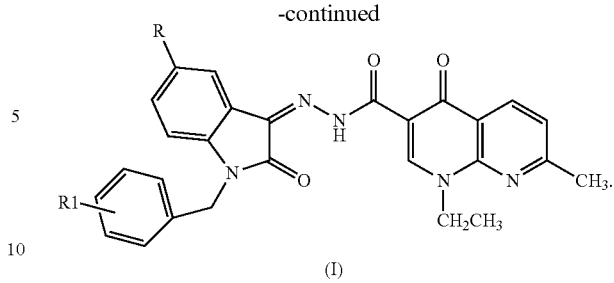
(I)
6. Method according to claim 5, wherein the reaction is under reflux.
* * * * *